(12) United States Patent
Sporrer

(10) Patent No.: US 10,195,635 B2
(45) Date of Patent: Feb. 5, 2019

(54) MULTICOMPONENT SINTERED POROUS LIQUID APPLICATOR NIBS

(71) Applicant: POREX CORPORATION, Fairburn, GA (US)

(72) Inventor: Kevin Sporrer, Sharpsburg, GA (US)

(73) Assignee: Porex Corporation, Fairburn, GA (US)

(*) Notice: Subject to any disclaimer, the term of this patent is extended or adjusted under 35 U.S.C. 154(b) by 108 days.

(21) Appl. No.: 15/415,111

(22) Filed: Jan. 25, 2017

(65) Prior Publication Data

US 2017/0209894 A1 Jul. 27, 2017

Related U.S. Application Data

(60) Provisional application No. 62/286,493, filed on Jan. 25, 2016.

(51) Int. Cl.

| | | |
|---|---|---|
| *B43K 5/00* | (2006.01) | |
| *B05C 1/02* | (2006.01) | |
| *A45D 34/04* | (2006.01) | |
| *A61B 17/00* | (2006.01) | |
| *A61K 8/02* | (2006.01) | |
| *A61K 9/00* | (2006.01) | |
| *A61L 26/00* | (2006.01) | |

(Continued)

(52) U.S. Cl.
CPC ............. *B05C 1/02* (2013.01); *A45D 34/04* (2013.01); *A45D 34/042* (2013.01); *A61B 17/00* (2013.01); *A61B 17/00491* (2013.01); *A61K 8/0204* (2013.01); *A61K 9/0014* (2013.01); *A61L 26/0061* (2013.01); *A61M 35/00* (2013.01); *A61M 35/006* (2013.01); *A61Q 1/04* (2013.01); *A61Q 1/10* (2013.01); *A61Q 3/04* (2013.01); *B05C 17/00* (2013.01); *B05D 1/28* (2013.01); *B43K 1/003* (2013.01); *B43K 1/006* (2013.01); *B43K 8/06* (2013.01); *C08J 9/24* (2013.01); *A61K 2800/872* (2013.01)

(58) Field of Classification Search
CPC ...................................................... B43K 1/006
USPC ............................................................ 401/196
See application file for complete search history.

(56) References Cited

U.S. PATENT DOCUMENTS

| | | | |
|---|---|---|---|
| 4,723,859 A | 2/1988 | Kitoh | |
| 8,141,717 B2 * | 3/2012 | Wingo | B01D 39/1661 210/500.22 |

(Continued)

FOREIGN PATENT DOCUMENTS

| | | |
|---|---|---|
| DE | 102008025883 | 12/2009 |
| EP | 2059556 | 5/2009 |

OTHER PUBLICATIONS

International Search Report and Written Opinion, PCT Patent Application No. PCT/US2017/014870, dated Apr. 20, 2017, 14 pages.

(Continued)

*Primary Examiner* — Jennifer C Chiang
(74) *Attorney, Agent, or Firm* — Kilpatrick Townsend & Stockton LLP

(57) ABSTRACT

A porous sintered multicomponent applicator nib and methods of making and using these nibs. The porous nibs are made from sintered plastic particles. These nibs are used with liquid applicators devices, medical devices, writing tools or cosmetic applicators to apply liquids containing high solids or pigments to surfaces such as metal, paper, skin, hair, tissue or a wound.

25 Claims, 5 Drawing Sheets

(51) Int. Cl.
*A61F 13/40* (2006.01)
*A61Q 1/04* (2006.01)
*A61Q 1/10* (2006.01)
*A61Q 3/04* (2006.01)
*B05D 1/28* (2006.01)
*B43K 1/00* (2006.01)
*A61M 35/00* (2006.01)
*B05C 17/00* (2006.01)
*B43K 8/06* (2006.01)
*C08J 9/24* (2006.01)

(56) References Cited

U.S. PATENT DOCUMENTS

| | | | |
|---|---|---|---|
| 8,308,388 B2 | 11/2012 | Guay | |
| 8,852,122 B2 * | 10/2014 | Mao | A61B 10/0045 600/563 |
| 8,920,339 B2 * | 12/2014 | Mao | A61B 10/0045 600/572 |
| 2011/0208136 A1 | 8/2011 | Sollingen et al. | |

OTHER PUBLICATIONS

International Preliminary Report on Patentability, PCT Patent Application No. PCT/US2017/014870, dated Aug. 9, 2018.

\* cited by examiner

MULTICOMPONENT SINTERED POROUS LIQUID APPLICATOR NIBS

PRIOR RELATED APPLICATION

This application claims the benefit of U.S. Provisional Application Ser. No. 62/286,493, filed Jan. 25, 2016, titled "Multicomponent Sintered Porous Liquid Applicator Nibs" the entire contents of which are hereby incorporated by reference.

FIELD OF THE INVENTION

The field of the present invention relates to porous sintered multicomponent applicator nibs and methods of making and using these nibs. The porous nibs have at least three components and are made by sintering polymeric particles. These nibs are used with liquid applicator devices, medical devices, writing tools or cosmetic applicators to apply liquids containing high solid content or high pigment content to surfaces such as metal, paper, skin, hair, tissue or a wound.

BACKGROUND

Sintered porous plastic and elastomeric media have been used as dye-based and low solid content liquid applicators for years. The liquid applicators include medical devices, writing instruments and cosmetic devices. Although sintered porous polymeric nibs are successful in dye-based and low solid content liquid applicators, such as highlighters, they have not been successful in applicators that use liquids with a high solid content, such as, viscous medical adhesives, dry erase inks, metallic inks, cosmetic formulations, eyeliner liquids, etc. What is needed are sintered polymeric porous nibs for use in high solid content liquid applicators or high solid pigment content liquid applicators.

BRIEF SUMMARY

The present invention provides a solution for using sintered polymeric porous nibs with liquids having high solid content or high solid pigment content. The present application solves the problems above and provides sintered porous polymeric multicomponent liquid applicator nibs and methods of making and using these nibs. In one embodiment, the multicomponent nibs comprise three sections, a shank, a nub and a head. In another embodiment, the multicomponent nibs comprise two sections, a shank and a head. The nibs are made from sintered porous polymeric media comprising plastic particles. The applicators employing nibs of the present invention provide surprisingly improved properties for dispensing high solid content liquids, such as high and consistent liquid flow for a prolonged time, low liquid leakage and a desired skin comfort in handling the applicator.

In one embodiment there is provided a porous multicomponent sintered nib comprising a porous shank, a porous nub, and a porous head, wherein the shank contacts a first end of the nub and the head contacts a second end of the nub, wherein the shank has a pore size that is greater than a pore size of the nub, and the nub has a pore size that is greater than a pore size of the head. It is possible for the nub to have a diameter that is larger than the shank diameter. The shank pore size may be from about 80 to about 150 microns. The nub pore size may be from about 30 to about 60 microns. The head pore size may be from about 10 to about 30 microns. Various porosities are also possible. The shank may have a porosity of from about 30 to about 50%. The nub may have a porosity of from about 30 to about 50%. The head may have a porosity of from about 30 to about 70%. In a specific version, the head has a greater porosity than the shank. The nub may have one or more vents that allow venting when the nub is positioned in an applicator.

In another embodiment there is provided a porous multicomponent sintered nib comprising a porous shank section and a porous head section. The nib's head section may comprise two components, a head tip and a head body, wherein the head tip component has a smaller pore size than the head body component. The head tip contacts a surface and may comprise a soft porous material and optionally elastomers. The head body may comprise relatively rigid materials. The porous shank may comprise two distinguishable components; a the shank head connection component which contacts the head body, and a shank reservoir connection component which contacts fluid in a reservoir of an applicator. The shank reservoir connection component has a higher pore size than the shank head connection component. In a specific embodiment, the head body component and shank head connection component have the same pore size and porosity. The shank pore size may be from about 80 to about 150 microns. The head pore size may be from about 10 to about 50 microns. Various porosities are also possible. The shank may have a porosity of from about 30 to about 50%. The head may have a porosity of from about 30 to about 70%. In a specific version, the head has a greater porosity than the shank.

Various materials are possible and considered within the scope of this disclosure. For example, the shank, nub, and head may be plastic particles. It is also possible for the head to contain plastic particles and elastomeric particles.

The nibs described herein may be used in connection with an applicator device. For example, the applicator may have a housing, a reservoir within the housing, and the nib positioned within the housing. The shank is generally located partially within the reservoir with the head extending beyond a wall or otherwise outside of the housing. The applicator may be used to apply high solids or pigments to a surface comprising. This may be done by exposing the shank of the nib to the liquid containing high solids or pigments in a reservoir; permitting capillary force to move the liquid from the reservoir into the shank, through the shank into the nub, through the nub into the head of the nib and to the tip of the head; contacting the tip of the head to the surface; and permitting the liquid to flow from the head onto the surface. The surface to which the liquid may be applied may be plastic, metal, paper, skin, hair, tissue or a wound. The liquid being applied may be a cosmetic, a medicine, an adhesive, an ink, an antiseptic, an antibacterial, an antibiotic, or a liquid therapeutic agent.

In nib embodiments containing a shank and a head, but no nub, the shank of the nib is exposed to the liquid containing high solids or pigments in a reservoir of an applicator; capillary forces move the liquid from the reservoir into the shank, through the shank into the head body and to the tip of the head. Then the tip of the head contacts a surface permitting the liquid to flow from the head onto the surface. The surface to which the liquid may be applied may be plastic, metal, paper, skin, hair, tissue or a wound. The liquid being applied may be a cosmetic, a medicine, an adhesive, an ink, an antiseptic, an antibacterial, an antibiotic, or a liquid therapeutic agent.

Other objects and advantages of the invention will be apparent from the following summary and detailed descrip-

DETAILED DESCRIPTION

Figure 1:
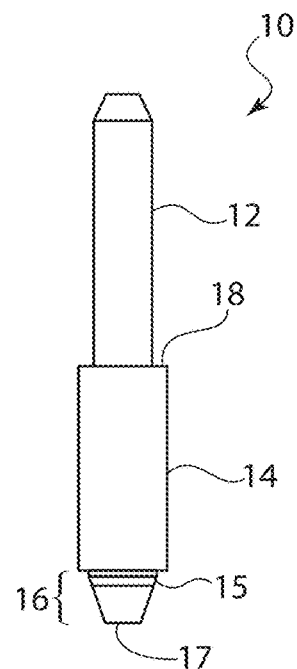
FIG. 1 shows a front plan view of a schematic representation of a structure of a multicomponent nib having three sections, a shank, a nub and a head.
Figure 2:
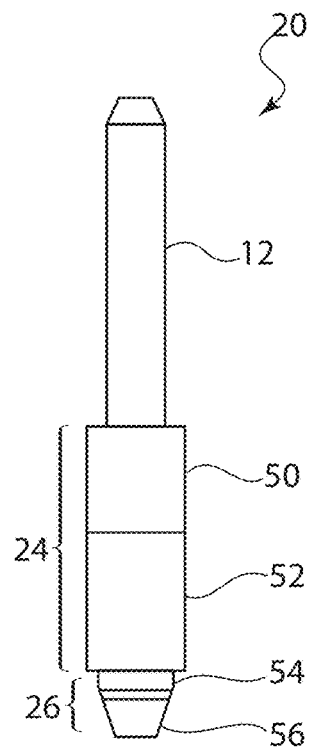
FIG. 2 shows a front plan view of a schematic representation of a nib having a two-part nub and a two-part head.
Figure 3:
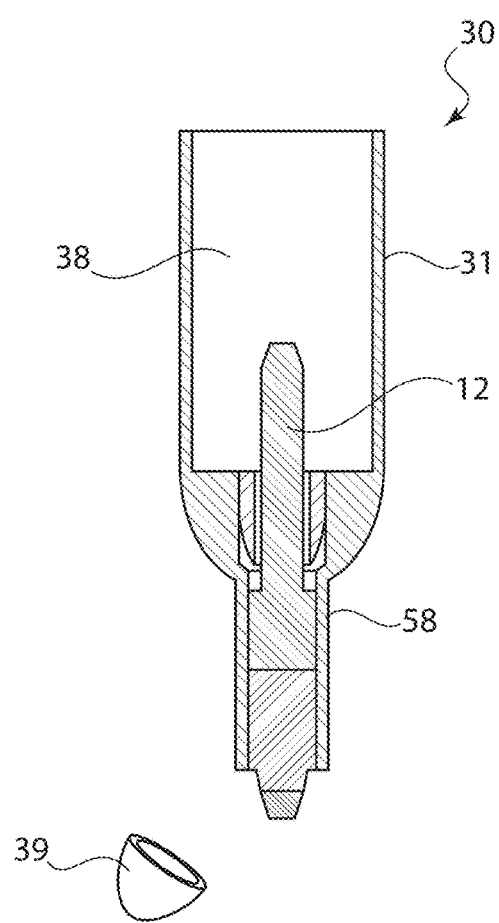
FIG. 3 is a cross-sectional view of the nib of FIG. 2 in a liquid applicator housing.

In some embodiments, the multicomponent porous nibs 10 disclosed herein generally have three primary sections: a shank 12, a nub 14 and a head 16. In some embodiments, the multicomponent porous nib has two primary sections: a shank and a head. As illustrated by FIGS. 1-3, the shank 12 is at a first end of nibs 10 and 20 and will extend into an ink reservoir 38 (FIG. 3). The nub 14 in FIG. 1 and nub 24 in FIG. 2 are in the middle of nib 10 or 20, respectively. Nubs provide mechanical coupling with an inner wall of an applicator housing 58 in FIG. 3. The head tip 17 of nib 10 and head tip 56 of the nib 20 in FIG. 2 are located at a second end of the nibs and provide direct contact with a surface for application of liquid. The body of nib 10 and nib 20, including shank, nub and head, are formed at the same time from polymeric particles through a co-sintering process. The nib 10 and nib 20 are a single piece porous media with distinguishable pore size components. The nib is formed in a single thermal sintering step and pores in the nib, including shank, nub and head are connected.

The nibs 10 have the following properties and structures. The first component with the largest pore size is a porous shank 12. The porous shank 12 is located at the shank end of the nib 10 that directly contacts liquids with a high solid content in a liquid reservoir. This component has the highest liquid flow rate and lowest capillary force. The first component is designed to draw the liquid from the liquid reservoir. The second component with medium pore size is called a nub 14. The nub 14 is located in the middle of the nib 10. The second component has a lower liquid flow rate and higher capillary force than the first component. The second component is designed to draw the liquid from the first component and prevent liquid dripping from the nib. The third component, called the head 16, with the lowest pore size, is at an end opposite the shank end of the nib. This third component has the lowest liquid flow rate but the highest capillary force. The third component is designed to draw the liquid from the second component and provides a comfortable writing experience and fine writing effect. This three-component nib design provides a consistent liquid application rate on a target surface and/or an excellent writing effect.

In one embodiment, the porous shank 12, the nub 14, and the head 16 of the multicomponent nib are made by sintering plastic particles. In another embodiment, the head 16 of the multicomponent nib is made by sintering plastic particles in combination with elastomeric particles.

The different components of the sintered porous multicomponent nib have distinguishable pore sizes, capillary forces and liquid flow rates. Nib components with smaller pore sizes have lower fluid flow rates and higher capillary force. Nib components with larger pore sizes have higher fluid flow rates and lower capillary force.

The present invention also provides a method for delivering liquids with high solid content onto a target surface using applicator devices containing the sintered porous multicomponent nib.

The present invention provides a liquid application device comprising the sintered porous multicomponent nib in an applicator housing. The nub of the multicomponent nib is configured within the housing in a manner to prevent leakage of the liquid.

In this application, the term multicomponent means a minimum of three components. Current commercial products have one or two components.

A component in the present invention means the distinguishable physical structures that comprise the same polymers, with relatively uniform pore size and porosity. The same polymers mean the polymers have the same chemical composition. For example, all polyethylenes, including high density polyethylene, low density polyethylene, and ultra high molecular weight polyethylene, are the same polymers. Polyethylene and polypropylene are different polymers because they have different chemical structures.

Figure 4A:
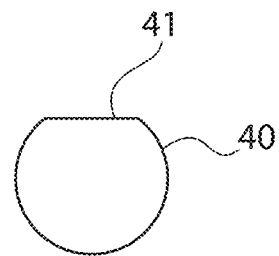
FIGS. 4A-4C show cross-sectional views of a nub with recessed regions which do not contact the inner wall of an applicator and serve as vents.
Figure 4B:
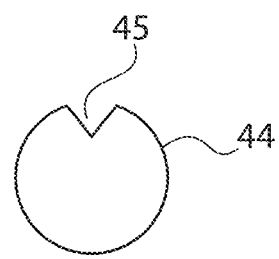
Figure 4C:
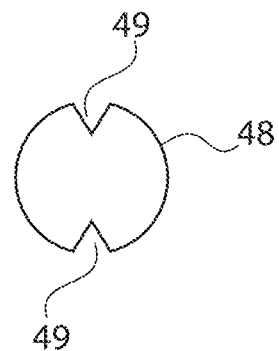

The multicomponent nibs of the present invention generally comprise three distinguishable sections, a shank 12, a nub 14 and a head 16 (the head may also be referred to as a "tip" herein, and the tip section is referred to as numeral 17). These three sections have their own functions. The shank 12 is for drawing the liquid from a liquid reservoir 38. The nub 14 is for attaching the applicator to the internal wall 58 of an applicator housing 31, as illustrated by FIG. 3. The nub 14 may have a small region (which may be one or more regions) which does not contact the inner wall of the housing in order to permit air to flow into the applicator 30 as fluid is dispensed. Examples of these regions are illustrated by FIGS. 4A-C (see 41, 45, 49). These regions act as vents. The head 16 is for applying liquid to the target surface. Target surfaces include, without limitation, plastic, metal, paper, canvas, skin, hair, tissue or a wound.

In some embodiments, the first component is related to the shank, the second component is related to the nub, and other components are related to the head.

Examples of high solid liquid application devices that may house the sintered porous polymeric multicomponent nib include, but are not limited to, viscous medical adhesive applicators, dry-erase markers, cosmetic applicators such as eyeliner pens, eyebrow pens, manicure pens, etc.

The components of the multicomponent applicators of the present invention have different capillary drawing forces. In different embodiments, the shank has a pore size of about 80 to about 150 microns, about 90 to about 140 microns or about 100 to about 130 microns. In various embodiments, the nub has a pore size of about 30 to about 60 microns, about 40 to about 60 microns, or about 50 to about 60 microns. In different embodiments, the head has a pore size of at least 10 microns, about 10 to about 30 microns, or about 15 to about 30 microns. In some embodiments, the pore sizes within a nub may be greater near the shank and lower near the head. The pore size of the shank is larger than the pore size of the nub and head. The pore size of the shank will depend on the liquid formula and liquid reservoir's capillary force. The capillary force of the shank should be strong enough to draw the liquid from the liquid reservoir at a consistent rate and also not affect the chemistry and solid component in the liquid solution. The shank diameter is typically smaller than the nub or head diameter and the flow in the shank has to be greater than or equal to the flow in the nub or head. For applicators used as writing instruments in the present invention, the pore size of the shank should be above 80 microns to provide adequate drawing force and sufficient liquid flow rate for the applicator. When the pore size of the shank is lower than 80 microns, even if the shank has a higher capillary force, it will not provide enough liquid flow for the applicator.

The pore size of the nub is smaller than the pore size of the shank, but larger than the pore size of the head. The pore size of the nub is optimized to provide multiple functions. The nub has a higher capillary force than the shank to draw the liquid from the shank and transmit the liquid to the head. The nub provides good mechanical strength for insertion and fixation into an applicator housing. The nub also has enough capillary force to prevent liquid from dripping through it due to gravity and negative environmental pressure.

The pore size of the head is smaller than the pore size of the shank and the nub. The pore size of the head provides strong capillary force to draw the liquid from the nub, although the pore size cannot be too small to decrease the liquid flow and filter out the solid component in the liquid. The smaller pore size of the head also provides a soft feel to a user when applying the free end of the head, the tip, to a target surface and provides more precise application of liquid to the target surface.

The design of multicomponent nibs of present invention provides optimized performance of high solid content liquid delivery and prevents liquid leakage under different application and storage conditions. The nibs have controlled capillary drawing force and flow resistance from the liquid reservoir into the shank, from the shank to the nub, and from the nub to the head.

In addition to these three components, more components can be added to the sintered porous polymeric multicomponent applicator nib to provide desired liquid delivery and application properties. One example is illustrated by FIG. 2. For example, the nib's head 26 may comprise two different components, such as a tip 56 and a body 54. The tip area 56 contacts a surface and may comprise a soft porous material. The body 54 may comprise relatively rigid materials. In another embodiment, the nub may comprise two distinguishable components with different pore sizes and porosities. In different embodiments of the present invention, the sintered porous polymeric multicomponent applicator may comprise four, five, six, seven, eight or more components.

The nub optionally contains at least one shallow area for air venting during the liquid application process. The diameter and depth of the vent is designed to allow enough air flow into the barrel and at the same time to prevent liquid from leaking between the nub and the inner wall of the applicator barrel. Examples of three nubs are shown in cross section in FIG. 4. In FIG. 4A, the nub 40 has a vent 41. In this example, vent 41 is provided as a generally flat surface on an otherwise cylindrically shaped cross-sectional nub. In FIG. 4B, an alternate nub 44 is shown having a notched vent 45. In FIG. 4C, a further nub 48 is shown having has two notched vents 49. Although notched vents are shown as generally be V-shaped from an otherwise cylindrically shaped cross-sectional nub, it should be understood that alternate shapes for cutouts are possible. For example, the vents may be curved, square or rectangular shaped, or have any other shape. Vents can optionally extend into the head.

Figure 6:
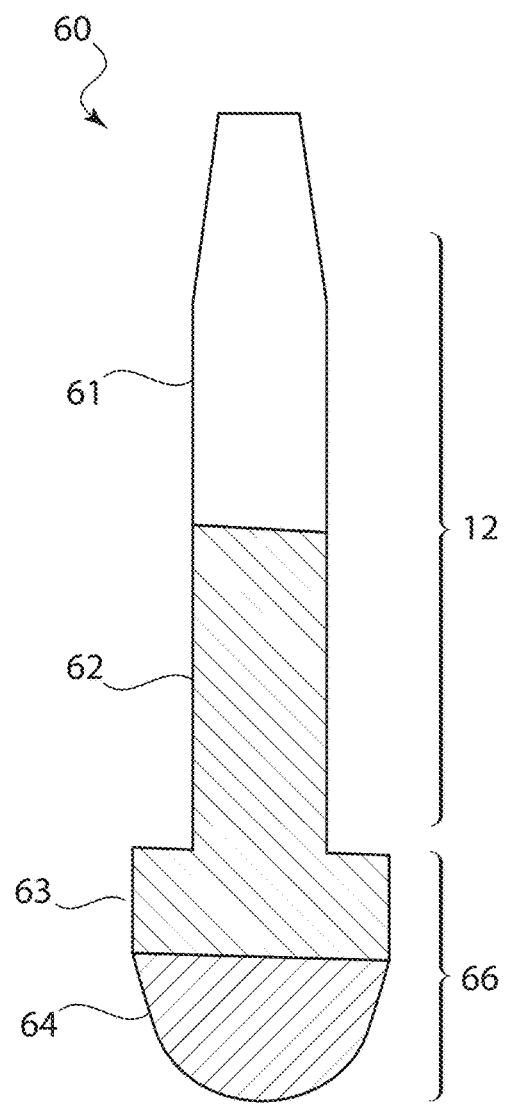
FIG. 6 shows a front plan view of a schematic representation of a structure of a multicomponent nib having two sections, a shank and a head.

In one embodiment a multicomponent nib has two sections, a shank section and a head section. One example is illustrated in FIG. 6. This nib 60 has a shank section 12 and a head section 66. The nib's head section 66 may comprise two components, a head tip 64 and a head body 63, wherein the head tip component 64 has a smaller pore size than the head body component 63. The head tip 64 contacts a surface and may comprise a soft porous material. The head body 63 may comprise relatively rigid materials. The shank 12 may comprise two distinguishable components; the shank head connection component 62 and the shank reservoir connection component 61. The shank reservoir connection component 61 extends into a reservoir of an applicator, contacts liquid and transmits the liquid through the shank reservoir connection component 61 and into the shank head connection component 62 which contacts the head body 63, permitting fluid to flow through the head body 63 and into the head tip 64. Upon contacting the head tip 64 with a surface, fluid flows from the head tip 64 onto the surface. The shank reservoir connection component 61 has a higher pore size than the shank head connection component 62. In a specific embodiment, the head body component 63 and shank head connection component 62 have the same pore size and porosity. In this embodiment, the shank contacts an inner wall of the applicator and frictionally fits into the applicator.

Fluids Containing High Solids

Inks containing high solids comprise more than 1% and up to 10% suspended pigment particles (% by volume) or at least 1%, 2% 3%, 4%, 5%, 6%, 7%, 8%, 9%, or 10%, suspended pigment particles. In some embodiments, inks containing high solids comprise more than 1% and up to 5% suspended pigment particles (% by volume).

A general ink composition for a dry erase marker is disclosed in US 20040182281, U.S. Pat. No. 6,031,023, and US 20100008711.

An ink formulation for a high solid-content liquid cosmetic is disclosed in WO2008145258 and in EP1462084A1.

Cosmetics containing high solids comprise more than 1% and up to 10% suspended solid particles (% by volume) or at least 1%, 2%, 3%, 4%, 5%, 6%, 7%, 8%, 9%, or 10%, suspended solid particles. In some embodiments, cosmetics containing high solids comprise more than 1% and up to 5%, more than 1% and up to 4.5%, more than 1% and up to 4%, suspended solid particles (% by volume).

A medical adhesive composition is disclosed in U.S. Pat. No. 7,094,250. Other fluids which may be applied with the applicators comprising the multicomponent nibs of the present invention include without limitation, antiseptics, antibacterials, antibiotics, adhesives, and other liquid therapeutics agents with high solid content.

In one specific embodiment, the sintered porous polymeric multicomponent applicator nib is made of sintered porous plastic. In yet another embodiment, the head of the porous multicomponent applicator nib is made of sintered porous plastic in combination with an elastomeric material. Inclusion of elastomeric materials generally increases compressibility of the nib head.

Sintered porous plastic materials generally are rigid and self-supporting. In some applications, a flexible and stretchable porous material is preferred for its flexibility and elasticity. In this case, one or more elastomeric materials are used in combination with sintered plastic particles in the head of the nib. Elastomeric materials that can be sintered with plastic particles into sintered porous elastomeric media are provided herein. In one embodiment, the sintered porous material of the nib head is made of mixtures of plastic and elastomeric materials to provide the heads of porous nibs with a variety of hardness, flexibility and durability. For example, the head of the nib may be made from mixtures of plastic materials and elastomeric materials in order to produce a sintered porous material with the desired rigidity and flexibility combination and to ensure that the feel on the hand is appropriate during use of the nib and application of the head tip to the surface. Potential ratios of plastic materials and elastomeric materials in the head of the nib can vary from 9.9 to 0.1, from 9.5:0.5 to 0.5:9.5, from 9:1 to 1:9; from 8:2 to 2:8, from 7.5 to 2.5 or from 7.0 to 3.0.

Many factors may affect the sintered porous polymeric material's pore size. These factors include the polymer's particle size, the polymer's properties, the sintering temperature and duration, the sintering pressure etc. In general, the larger polymer particles will produce a larger the pore size.

Thermoplastic Materials that can be Used to Make Multicomponent Porous Nibs

Plastics suitable for use in multicomponent porous nibs of the present invention, in some embodiments, comprise polyolefins, polyamides, polyesters, rigid polyurethanes, polyacrylonitriles, polycarbonates, polyvinylchloride, polymethylmethacrylate, polyvinylidene fluoride, polytetrafluoroethylene, polyethersulfones, polystyrenes, polyether imides, polyetheretherketones, or polysulfones, and combinations and copolymers thereof. One or more plastics may be used in the multicomponent porous nibs of the present invention.

In some embodiments, a polyolefin comprises polyethylene, polypropylene, and/or copolymers thereof. Polyethylene, in one embodiment, comprises high density polyethylene (HDPE). High density polyethylene, as used herein, refers to polyethylene having a density ranging from about 0.93 g/cm$^3$ to about 0.97 g/cm$^3$. Polyethylene, in one embodiment, comprises medium density polyethylene. Medium density polyethylene (MDPE), as used herein, refers to polyethylene having a density ranging from about 0.92 g/cm$^3$ to about 0.93 g/cm$^3$. Polyethylene, in one embodiment, comprises low density polyethylene. Low density polyethylene (LDPE), as used herein, refers to polyethylene having a density ranging from about 0.91 g/cm$^3$ to about 0.92 g/cm$^3$. Polyethylene, in one embodiment, comprises linear low density polyethylene. Linear low density polyethylene (LLDPE), as used herein, refers to polyethylene having a density ranging from about 0.91 g/cm$^3$ to about 0.92 g/cm$^3$. Polyethylene, in one embodiment, comprises very low density polyethylene. Very low density polyethylene (VLDPE), as used herein, refers to polyethylene having a density ranging from about 0.89 g/cm$^3$ to about 0.91 g/cm$^3$. In another embodiment, polyethylene comprises ultrahigh molecular weight polyethylene (UHMWPE). Ultrahigh molecular weight polyethylene, as used herein, refers to polyethylene having a molecular weight greater than 1,000,000. In another embodiment, polyethylene comprises very high molecular weight polyethylene (VHMWPE). Very high molecular weight polyethylene, as used herein, refers to polyethylene having a molecular weight greater than 300,000 and less than 1,000,000. In another embodiment, polyethylene, in this invention can be cross-linked polyethylene.

Elastomeric Materials Optionally Used with Plastic in the Head of the Multicomponent Porous Nibs Elastomers suitable for use in combination with plastic particles in the head of the multicomponent porous nibs of the present invention, according to some embodiments, comprise thermoplastic elastomers (TPE). Thermoplastic elastomers comprise polyurethanes and thermoplastic polyurethanes (TPU). Thermoplastic polyurethanes, in some embodiments, include multiblock copolymers comprising a polyurethane and a polyester or polyether.

In other embodiments, elastomers suitable for use in combination with plastic particles in the head of the multicomponent porous nibs of the present invention comprise polyisobutylene, polybutenes, butyl rubber, or combinations thereof. In another embodiment, elastomers comprise copolymers of ethylene and other monomers such as ethylene-propylene copolymer, referred to as EPM, ethylene-octene copolymer, and ethylene-hexene copolymer. In another embodiment, elastomers comprise copolymers of propylene and other monomers such as ethylene-propylene copolymer, referred to as EPM, ethylene-octene copolymer, and polyethylene-hexene copolymer. In a further embodiment, elastomers comprise chlorinated polyethylene or chloro-sulfonated polyethylene. In a further embodiment, elastomers comprise ethylene vinyl acetate (EVA).

In some embodiments, elastomers suitable for use in combination with plastic particles in the head of the multicomponent porous nibs of the present invention comprise 1,3-dienes and derivatives thereof 1,3-dienes include styrene-1,3-butadiene (SBR), styrene-1,3-butadiene terpolymer with an unsaturated carboxylic acid (carboxylated SBR), acrylonitrile-1,3-butadiene (NBR or nitrile rubber), isobutylene-isoprene, cis-1,4-polyisoprene, 1,4-poly(1,3-butadiene), polychloroprene, and block copolymers of isoprene or 1,3-butadiene with styrene such as styrene-ethylene-butadiene-styrene (SEBS) or hydrogenated SEBS. In other embodiments, elastomers comprise polyalkene oxide polymers, acrylics, or polysiloxanes (silicones) or combinations thereof.

In a further embodiment, elastomers suitable for use in combination with plastic particles in the head of the multicomponent porous nibs of the present invention, in some embodiments, comprise Forprene®, Laprene®, Skypel®, Skythane®, Synprene®, Rimflex®, Elexar®, Flexalloy®, Tekron®, Dexflex®, Typlax®, Uceflex®, Dexflex®, Engage®, Hercuprene®, Hi-Fax®, Innopol®, Novalene®, Kraton®, Muti-Flex®, Evoprene®, Hytrel®, Nordel®, Versify®, Vistamaxx®, Viton®, Vector®, Silastic®, Santoprene®, Elasmax®, Affinity®, Attane®, Septon® and Sarlink®.

Sintered polymeric elastomeric and plastic materials in the head of the nib according to some embodiments of the present invention are porous. In one embodiment, for example, a sintered polymeric elastomeric and plastic material has a porosity ranging from about 10% to about 90%. In another embodiment, a sintered polymeric elastomeric and plastic material has a porosity ranging from about 20% to about 80% or from about 30% to about 70%. In a further embodiment, a sintered polymeric elastomeric and plastic material in the nib head has a porosity ranging from about 40% to about 60%. The porosity range for the shank is about 30% to about 50%. The porosity range for the nub is about 30% to about 50%.

The head of a sintered porous polymeric multicomponent nib, according to some embodiments of the present invention, comprises at least one elastomer in an amount ranging from about 0 weight percent (wt. %) to about 30 wt. %, about 5 wt. % to about 30 wt. % or about 10 wt. % to about 30 wt. %. In other embodiments, the head comprises at least one elastomer in an amount ranging from about 2 wt. % to about 20 wt. %. In another embodiment, the head comprises at least one elastomer in an amount ranging from about 5 wt. % to about 20 wt. %. In these embodiments, plastic constitutes the remainder or the majority of the remainder of the sintered polymeric material. In some embodiments, more than one plastic may be combined with an elastomer in the head.

Properties of the Components of the Multicomponent Porous Nibs

The components of the multicomponent porous nibs of the present invention have different ranges of pore sizes. The pore sizes of the shank, nub and head are generally between about 80 microns to about 150 microns. The shank has a pore size of about 80 to about 150 microns, about 90 to about 140 microns or about 100 to about 130 microns. The nub has a pore size of about 30 to about 60 microns, about 40 to about 60 microns, or about 50 to about 60 microns. The head has a pore size of at least 10 microns, about 10 to about 30 microns, or about 15 to about 30 microns. In some embodiments, the pore size of a nub may be greater near the shank and lower near the head.

Methods of Making Multicomponent Porous Nibs

In one embodiment, providing a sintered porous multicomponent nib comprises providing a plurality of polymeric particles into a mold cavity and sintering the polymeric particles.

Polymeric particles in this invention include plastic particles, elastomeric particles and combination of plastic and elastomeric particles for use in the head of the nib.

Polymeric particles, in some embodiments, have average sizes ranging from about 1 µm to about 1 mm. In another embodiment, polymeric particles have average sizes ranging from about 10 µm to about 900 µm, from about 50 µm to about 500 µm, or from about 100 µm to about 400 µm. In a further embodiment, polymeric particles have average sizes ranging from about 200 µm to about 300 µm. In some embodiments, polymeric particles have average sizes less than about 1 µm or greater than about 1 mm.

Polymeric particles, in some embodiments, are sintered at a temperature ranging from about 94° C. to about 370° C. In some embodiments, polymeric particles are sintered at a temperature ranging from about 150° C. to about 260° C. In some embodiments, polymeric particles are sintered at a temperature ranging from about 165° C. to about 205° C. The sintering temperature, according to embodiments of the present invention, is dependent upon and selected according to the identity of the polymeric particles.

Polymeric particles, in some embodiments, are sintered for a time period ranging from about 30 seconds to about 30 minutes. In other embodiments, polymeric particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of polymeric particles is administered under ambient pressure (1 atm). In other embodiments sintering of polymeric particles is administered under pressures greater than ambient pressure.

One of ordinary skill in the art knows to vary the sintering temperature and duration depending on the size of the object and the material.

The tricomponent nib of present invention was made by making a metal mold having a cavity with the shape of the tricomponent nib; filling the head section of the cavity with plastic particles having an average particle size from 30 microns to about 150 microns; filling the nub section of the cavity with plastic particles having average particle size from 150 microns to about 250 microns; filling the shank part of the cavity with plastic particles having average particle size from 250 microns to about 500 microns; sintering the plastic particles inside the mold cavity at a desired temperature and time to form tricomponent nibs with three distinguishable pore size components. The temperature depends on the polymer particle composition, for polyethylene, 140° C. to 190° C. are commonly employed temperatures as known to one of skill in the art. The sintering time depends on the part size, larger parts require longer sintering times. Sintering times can range from 2 minutes to 15 minutes.

In a specific embodiment, the plastic particles are polyethylene, including HDPE, VHMWPE and UHMWPE.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

A Three Component Nib

Some multicomponent nibs of the present invention have three sections, a shank section, a nub section and a head section. In this example, the multicomponent nib's three components are the same as the nib's three sections as there is only one pore size component in each section. The shank section is the large pore size component, the nub section is the medium pore size component and the head section is the small pore size component.

A three component writing instrument nib 10 of FIG. 1 has a shank section 12, a nub section 14 and a head section 16. The shank section 12 may generally be in the form of an elongated rod. Although it is envisioned that the shank section has a generally circular cross-section, it should be understood that other cross-sectional shapes are possible and are considered within the scope of this disclosure. The length of the shank section 12 may be similar to or longer than the nub section. In one example, the length of the shank section is from 5 mm to 50 mm, from 10 mm to 40 mm, or from 15 mm to 30 mm. As illustrated in FIG. 1, the diameter of the shank 12 may be is smaller than the diameter of the nub 14. In one example, the diameter of the shank is from 2 mm to 10 mm, from 3 mm to 9 mm, or from 4 mm to 8 mm. The shank section 12 is the first component and has an average pore size greater than about 80 microns.

In contact with the shank section 12 is the nub section 14. The nub section 14 is generally provided as having a larger diameter than the shank diameter. The result is a shoulder section 18 between the shank 12 and the nub 14 that creates a ledge-like feature. This ledge-like feature is for shank insertion into the reservoir and securing the nib in the correct position in applicator devices. In a specific example, the nub's length may vary from 2 mm to 20 mm. The nub's diameter may vary from 3 mm to 20 mm. The nub 14 is the second component and has an average pore size from about 40 microns to about 80 microns.

Adjacent to the nub section 14 is the head section 16. The head section is generally provided as having a tapered or conical end or head tip 17. The head cross-section at its nub-contacting end 15 is generally larger than the tip cross-section at its tip end 17. The head section 16 is the third component and has an average pore size from about 10 microns to about 30 microns.

In use, the nib 10 is placed into a housing 31 of an applicator 30, similar to the arrangement shown in FIG. 3. The nub is for attaching the applicator to the narrowed internal wall 58 of the applicator housing 31. The shank 12 is exposed to fluid located in the reservoir 38 in the lumen of the applicator. The fluid is permitted to flow through the shank 12, through the nub 14, and into the head 16. An individual applies the tip 17 of the head 16 (which extends outside the applicator housing 31) to a writing surface or other surface to which the fluid is to be applied. In a specific example, the nib 10 may be used in connection with a dry erase marker. In other examples, the nib may be used in connection with permanent or washable markers, an eye-liner applicator, a liquid medicine applicator, or any other example described herein.

Tricomponent nib 10 was made by making a metal mold with a cavity resembling the shape of the tricomponent nib 10; filling the head section of the cavity with UHMWPE particles having an average particle size of 120 microns; filling the nub section of the mold cavity with a mixture of 50% HDPE and 50% UHMWPE particles (wt. %) having an average particle size of about 200 microns; filling the shank section of mold cavity with HDPE particles having an average particle size of about 500 microns; sintering the polymer particles in the mold cavity at 170° C. for 5 minutes and cooling the mold to room temperature. The formed tricomponent nibs 10 have an average pore size of about 100 microns and 40% porosity in the shank component, an average pore size of about 50 microns and 40% porosity in the nub component, and an average pore size of about 30 microns and 60% porosity in the head component.

Example 2

A Multicomponent Nib Having a Two-Part Nub and/or a Two-Part Head

In this example, the multicomponent nib's three sections are not the same as the three pore size components. The shank 12 section, and part of the nub section 50 are large pore size components (larger than 80 microns); part of the nub section 52 and part of the head section 54 are medium pore size components (40 microns to 80 microns). Only the tip of the head section 56 is a small pore size component (10 microns to 30 microns).

Another embodiment of a multicomponent nib 20 is illustrated by FIG. 2. This nib 20 has a shank section 12, a nub section 24 and a head section 26. The nub section 24 and the head section 26 are formed from more than one component. Although the nub section 24 and head section 26 are shown together on the same nib 20, it should be understood that either section may be interchanged with the nub 14 and/or the head 16 described above in Example 1.

In this example, the nub section 24 comprises two components: a shank connection component 50 and a head connection component 52. The head component 26 also comprises two components, a body 54 and a tip 56.

The shank component 12 and nub's shank connection component 50 form the first component and have an average pore size greater than about 80 microns. The nub's head connection component 52 and the head body 54 form the second component, wherein the second component has an average pore size from about 40 microns to about 80 microns. The tip 56 of the head component 26 is part of the third component and has an average pore size from about 10 micron to about 30 microns.

Tricomponent nib 20 was made by making a metal mold with a cavity resembling the shape of tricomponent nib 20; filling the head tip section 56 of the mold cavity with UHMWPE particles having an average particle size of 80 microns; filling the head body section 54 and the nub's head connection section 52 of the mold cavity with a mixture of 50% HDPE and 50% UHMWPE particles (wt. %) having an average particle size of about 200 microns; filling the nub section 50 and shank section 12 of the mold cavity with HDPE particles having an average particle size of about 450 microns; sintering the polymer particles in the mold cavity at 170° C. for 5 minutes and cooling the mold to room temperature. The formed nibs 20 have an average pore size of about 90 microns and 40% porosity for shank component 12 and nub's shank connection component 50; an average pore size of about 50 microns and 40% porosity for the nub's head connection component 52 and head body 54; and an average pore size of about 20 microns and 60% porosity for the head tip component 56.

In use, the nib 20 is placed into an applicator 30. An applicator housing 31 with a nib placed therein is shown in cross section in FIG. 3. The shank 12 is exposed to fluid located in the lumen 38 of the applicator. The nub is for attaching the applicator to the narrowed internal wall 58 of the applicator housing 30 through a frictional fit. The fluid is permitted to flow through the shank 12, the nub and the head. An individual applies the tip of the head (which extends outside the applicator housing 30) to a writing surface or other surface to which the fluid is to be applied. In a specific example, the nib 20 may be used in connection with a dry erase marker. In other examples, the nib may be used in connection with permanent or washable markers, an eye-liner applicator, a liquid medicine applicator, or any other example described herein. A cap 39 may be optionally placed over the tip of the head and makes frictional contact with the housing 31.

Example 3

A Three-Component Nib for a Medical Adhesive Applicator Device

It should be understood that either of the nibs 10 or 20 described in the above examples may be used in connection with a medical adhesive applicator device. The three component nib shown in FIG. 2 has a shank section 12, a shaped nub section 24 and a conically shaped head section 26. The nib may be placed into a housing 31 as shown in FIG. 3. The fluid provided in the lumen 38 of the applicator 30 may be a medical adhesive. In use, the shank is exposed to the medical adhesive located in the lumen 38 of the applicator. The medical adhesive is permitted to flow through the shank, the nub and the head. A health care professional applies the tip of the head 56 outside the housing to a cutaneous wound of a patient to deposit medical adhesive and facilitate closure of the wound.

Example 4

A Three-Component Nib for a Cosmetic Applicator Device

It should be understood that either of the nibs 10 or 20 described in the above examples may be used in connection with a cosmetic applicator device. The nib may be placed into a housing 31 as shown in FIG. 3. The fluid provided in the lumen 38 of the applicator 30 may be a cosmetic fluid. In use, the shank is exposed to liquid containing pigment or other chemicals located in the lumen of the applicator. The cosmetic fluid is permitted to flow through the shank, the nub and the head. An individual applies the tip of the head outside the housing to the eyelids or other location to deposit the liquid for cosmetic purposes. The cosmetic liquid may be liquid eyeliner, liquid lip liner, liquid nail polish remover, or any other appropriate cosmetic liquid suitable for delivery as described herein.

Example 5

Leakage Test for Bicomponent and Tricomponent Nibs.

Writing instruments must not leak ink when they are not in use. Writing instruments must also not leak ink under negative environmental pressures. The tricomponent nibs of the present invention and a traditional bicomponent nib were compared for their leakage properties.

The testing markers were made by replacing the nib in the commercially available EXPO® dry eraser marker (Newell Office Brands, Atlanta, Ga., USA) and Crayola black dry erase marker (Crayola LLC, Easton Pa., USA) with a tricomponent nib or a bicomponent nib. The newly assembled test markers with new nibs were covered with the caps and stored at room temperature for at least 24 hours before testing.

Marker containing a tricomponent nib: Tricomponent nib configured as in FIG. 2, where components 12 and 50 are HDPE having an average pore size of 90 microns and porosity of about 40%; components 52 and 54 are a mixture of HDPE and UHMWPE having an average pore size of 50 microns and porosity of about 40%; component 56 is UHMWPE having an average pore size of 20 microns and porosity of about 60%; were assembled in a EXPO® dry eraser maker with a red ink reservoir and a Crayola dry erase marker with a black ink reservoir Marker containing a bicomponent nib: Bicomponent nib configured as in FIG. 2, where a first component of sections 12, 50, 52 and 54 are HDPE having an average pore size of about 90 microns and porosity of about 40%; and a second component in section 56 is UHMWPE having an average pore size of about 20 microns and porosity of about 60%; were assembled in an EXPO® dry eraser marker with a red ink reservoir or a Crayola dry erase marker with black ink reservoir.

The markers containing a tricomponent nib or a bicomponent nib were put into a vacuum oven vertically with the nib head facing down. The vacuum oven was pumped down to −0.5 bar and kept at this −0.5 bar vacuum pressure. An observer watched for ink dropping onto the vacuum oven floor within 30 seconds. Leaking was defined by observing a drop of ink leaking from the nib to the vacuum oven floor. The marker containing the bicomponent nib showed ink leakage from the nib and the marker containing the tricomponent nib did not show ink leakage from the nib.

Example 6

Write Out Test for Dry Eraser Makers Containing a Fiber Nib, a Bicomponent Nib or a Tricomponent Nib.

Writing instruments, including dry eraser markers, must deliver ink fast and consistently. The tricomponent nibs of the present invention and traditional bicomponent nibs were compared for their write out properties.

The testing markers were made by replacing the nib of a commercial EXPO® dry eraser marker (Newell Office Brands, Atlanta, Ga., USA) with a tricomponent nib of example 2 of the present invention and a traditional bicomponent nib (described below). The newly assembled test markers with new nibs were covered with the caps and stored at room temperature for at least 24 hours before testing.

Multicomponent nibs of example 2 were used for testing.

Bicomponent nibs with the configuration of FIG. 2, wherein the first component includes sections 12, 50, 52 and 54 of 50% HDPE and 50% UHMWPE having an average pore size of 50 microns and 40% porosity; and the second component 56 is UHMWPE having an average pore size of 20 microns and 60% porosity. This is a traditional bicomponent nib.

The conventional fiber nib is a commercially available EXPO® product and was used without modification. It was made from polyester fibers and had a pore size of approximately 30 microns. The fiber nib has aligned fibers which enables fluid flow in a straight line through a pore analogous to travelling through a straight pipe or straw.

The testing markers containing a tricomponent nib, a bicomponent nib and a fiber nib were put onto a Hutt HST10 write out testing machine (Essem International Co., Ltd. Bangkok, Thailand). The write out test was done at a force of about 100 gm, a speed of about 4 meter/minute and a line width of about 5 mm. The paper was polypropylene film coated paper for simulating a whiteboard condition. The markers were weighed before the write out test and at about every 25 meters during the writing. The markers weights were recorded and the uniformities in the written lines were observed.

Figure 5:
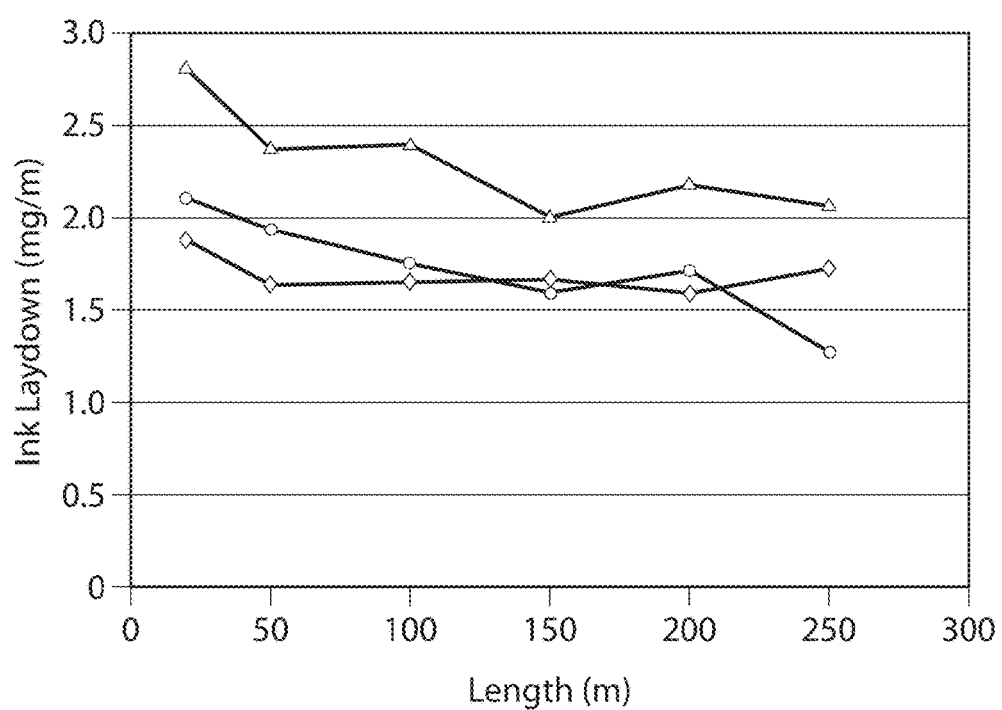
FIG. 5 illustrates comparative test results of ink deposition (mg/m) from markers containing a sintered plastic porous tricomponent nib of the present invention (solid triangle symbol), a bicomponent nib (solid circle symbol) and a polyester fiber nib (solid diamond symbol).

FIG. 5 shows the results of the write out test for the commercial expo dry eraser marker with fiber nibs (solid diamond), a dry eraser marker containing a tricomponent nib (solid triangle) and a dry eraser marker containing a bicomponent nib (solid circle). The results show that dry eraser marker containing a tricomponent nib provided a higher amount of initial ink delivery and an overall faster ink delivery performance during the 250 meter test. The ink laydown in the figure (milligram per meter (mg/m)) is for an average ink (mg) for one meter length of a 1 mm wide writing line. Since each nib had a different size and shape, the data are normalized to average 1 mm line width.

Example 7

A Multicomponent Nib Having a One Component Shank, One Component Nub and Two-Component Plastic Head Another embodiment of a multicomponent nib 20 is illustrated by FIG. 2. This nib 20 has a shank section 12, a nub section 24 and a head section 26, wherein the shank section 12 and the nub section 24 are a single component and the head section comprises two components, a body 54 and a tip 56.

The multicomponent nib of this example is made by making a metal mold with a cavity with the shape of nib 20; filling the head tip section 56 of the mold cavity with UHMWPE particles having an average particle size of 30 microns; filling the head body section 54 of the mold cavity with UHMWPE particles with an average particle size of 80 microns; filling the nub section 52 and nub section 50 of the mold cavity with HDPE and UHMWPE particles having an average particle size of about 200 microns; filling the shank section 12 of the mold cavity with HDPE particles having an average particle size of about 450 microns; sintering the polymer particles in the mold cavity at 170° C. for 5 minutes and cooling the mold to room temperature. The formed nibs 20 have an average pore size of about 90 microns and 40% porosity in shank component 12; an average pore size of about 50 microns and 40% porosity in nub components 52 and 50; an average pore size of about 20 microns and 60% porosity in the head body component 54 and an average pore size of about 10 microns and 40% porosity in the head tip component 56.

Example 8

A Nib Having a Two-Component Nub and a Two-Component Plastic Head

Another embodiment of a multicomponent nib 20 is illustrated by FIG. 2. This nib 20 has a shank section 12, a nub section 24 and a head section 26. The nub section 24 and head section 26 are formed from more than one component.

In this example, the nub section 24 comprises two components: a shank connection component 50 and a head connection component 52. The head section 26 also comprises two components, a body 54 and a tip 56.

The multicomponent nib of this example with the configuration of FIG. 2 is made by making a metal mold a cavity with the shape of nib 20; filling the head tip section 56 of the mold cavity with UHMWPE particles having an average particle size of 30 microns; filling the head body section 54 of the mold cavity with UHMWPE particles with an average particle size of 80 microns; filling the nub section 52 of the mold cavity with HDPE and UHMWPE particles having an average particle size of about 200 microns; filling the nub section 50 and shank section 12 of the mold cavity with HDPE particles having an average particle size about 450 microns; sintering the polymer particles in the mold cavities at 170° C. for 5 minutes and cooling the mold to room temperature. The formed nibs 20 have an average pore size of about 90 microns and 40% porosity in shank 12 and nub's shank connection component 50; an average pore size of about 50 microns and 40% porosity in nub head connection component 52; an average pore size of about 20 microns and 60% porosity in the head body component 54 and an average pore size of about 10 microns and 40% porosity in the head tip component 56.

Example 9

A Three Component Nib with an Elastomeric Head

Tricomponent nib 10 is made by making a metal mold a cavity in the shape of tricomponent nib 10; filling head section 16 of the mold cavity with a mixture of 95% UHMWPE particles having an average particle size of 80 microns and 5% ground Kraton® particles (wt. %) with an average particle size of about 80 microns; filling the nub section 14 of the mold cavity with 50% HDPE and 50% UHMWPE particles (wt. %) having an average particle size of about 200 microns; filling the shank section 12 of the mold cavity with HDPE particles having average particle size about 500 microns; sintering the polymer particles in the mold cavity at 170° C. for 5 minutes and cooling the mold to room temperature. The formed nibs 10 have an average pore size of about 100 microns and 40% porosity in shank component 12, an average pore size of about 50 microns and 40% porosity in nub component 14, and an average pore size of about 20 microns and 60% porosity in head component 16.

Example 10

A Multicomponent Nib with Plastic Head Body and Elastomeric Head Tip

Multicomponent nib 10 is made by making a metal mold a cavity with the shape of tricomponent nib 10; filling head tip section 17 of the mold cavity with a mixture of 95% UHMWPE particles (wt. %) having an average particle size of 80 microns and 5% ground Kraton® particles with an average particle size of about 80 microns; filling the head body section 15 of the mold cavity with UHMWPE particles having an average particle size of 120 microns; filling the nub section 14 of the mold cavity with 50% HDPE and 50% UHMWPE (wt. %) particles having an average particle size of about 200 microns; filling the shank section 12 of the mold cavity with HDPE particles having average particle size about 500 microns; sintering the polymer particles in the mold cavity at 170° C. for 5 minutes and cooling the mold to room temperature. The formed nibs 10 have an average pore size of about 100 microns pore size and 40% porosity in shank component 12, an average pore size of about 50 microns and 40% porosity for nub component 14, and an average pore size of about 30 microns and 40% porosity for head body component 15; and an average pore size of about 20 microns and 60% porosity in head tip component 17.

Example 11

A Nib Having a Two-Component Nub and/or a Two-Component Head and Head Tip Comprising Elastomeric Materials.

Another embodiment of a multicomponent nib 20 is illustrated by FIG. 2. This nib 20 has a shank section 12, a nub section 24 and a head section 26. Nub section 24 and head section 26 are formed from more than one component.

In this example, the nub section 24 comprises two components: a shank connection component 50 and a head connection component 52. The head section 26 also comprises two components, a body 54 and a tip 56. Tip 56 comprises elastomeric materials.

The multicomponent nib 20 is made by making a metal mold with a cavity with the shape of nib 20; filling head tip section 56 of the mold cavity with UHMWPE particles with an average particle size of 80 microns and 5% ground Kraton® elastomer particles (wt. %) having an average particle size of 100 microns; filling the head body section 54 of the mold cavity with UHMWPE particles with an average particle size of 80 microns; filling the nub section 52 of the mold cavity with HDPE and UHMWPE particles having an average particle size of about 200 microns; filling the nub shank connection section 50 and shank 12 of the mold cavity with HDPE particles having an average particle size about 450 microns; sintering the polymer particles in the mold cavity at 170° C. for 5 minutes and cooling the mold to room temperature. The formed nibs 20 have an average pore size of about 90 microns and 40% porosity for shank component 12 and nub's shank connection component 50; an average pore size of about 50 microns and 40% porosity for nub head connection component 52; an average pore size of about 20 microns and 60% porosity for head body component 54 and an average pore size of about 20 microns and 60% porosity for head tip component 56.

Example 12

A Multicomponent Nib Having a Two-Component Shank and a Two-Component Head

In this example, the multicomponent nib 60 does not have a nub section but does have a shank section 12 and a head section 66 (FIG. 6). The shank section 12 and the head section 66 are formed from more than one component. The shank 12 section has two components, a shank component 61 which contacts fluid in a reservoir, and a shank component 62 which contacts the head section. The head section 66 also comprises two components, a body 63 and a tip 64.

The shank section 61 has large pore size components (larger than 80 microns). Part of the shank section 62 and part of the head section 63 have medium pore size components (40 microns to 80 microns). Only the tip 64 of the head section has a small pore size component (10 microns to 30 microns).

The shank reservoir component 61 forms the first component and has an average pore size greater than about 80 microns. The shank head connection component 62 and the head body component 63 form the second component, wherein the second component has an average pore size from about 40 microns to about 80 microns. The tip 64 of the head section 66 is part of the third component and has an average pore size from about 10 micron to about 30 microns.

Liquid in a reservoir of an applicator moves through the shank reservoir component 61 into the shank head connection component 62 and next into the head body 63 and head tip 64. Liquid flows from the head tip 64 onto a surface upon application of the head tip 64 to the surface. In this embodiment, the shank contacts an inner wall of the applicator and frictionally fits into the applicator.

Tricomponent nib 60 was made by making a metal mold with a cavity resembling the shape of tricomponent nib 60; filling the head tip section 64 of the mold cavity with UHMWPE particles having an average particle size of 80 microns; filling the head body section 63 and the shank head connection section 62 of the mold cavity with a mixture of 50% HDPE and 50% UHMWPE particles (wt. %) having an average particle size of about 200 microns; filling the shank reservoir section 61 of the mold cavity with HDPE particles having an average particle size of about 450 microns; sintering the polymer particles in the mold cavity at 170° C. for 5 minutes and cooling the mold to room temperature. The formed nibs 60 have an average pore size of about 90 microns and 40% porosity for the shank reservoir component 61; an average pore size of about 50 microns and 40% porosity for the shank head connection component 62 and head body component 63; and an average pore size of about 20 microns and 60% porosity for the head tip component 64.

It is to be understood that the nib 60 described in this example may be used in any of the applicators mentioned above for applying medicines, cosmetics, inks or other high solid content liquid or high pigment content liquid.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

What is claimed is:

1. A porous sintered nib comprising:
a porous shank;
a porous nub; and,
a porous head, wherein the shank contacts a first end of the nub and the head contacts a second end of the nub, wherein the shank has an average pore size that is greater than an average pore size of the nub, and the nub has an average pore size that is greater than an average pore size of the head.

2. The nib of claim 1, wherein the shank comprises a shank diameter and the nub comprises a nub diameter, wherein the nub diameter is larger than the shank diameter.

3. The nib of claim 1, wherein the shank has an average pore size of from about 80 to about 150 microns, the nub has an average pore size of from about 30 to about 60 microns, and the head has an average pore size of from about 10 to about 30 microns.

4. The nib of claim 1, wherein the shank has a porosity of from 30% to 50%, the nub has a porosity of from 30% to 50%, and the head has a porosity of from 30% to 70%.

5. The nib of claim 1, wherein the head has a greater porosity than the nub and the shank.

6. The nib of claim 1, wherein the nub comprises one or more vents.

7. The nib of claim 1, wherein the nub comprises a shank connection section and a head connection section.

8. The nib of claim 1, wherein the head comprises a body and a tip.

9. The nib of claim 1, wherein the shank, the nub and the head comprise plastic particles.

10. The nib of claim 1, wherein the head comprises plastic particles and elastomeric particles.

11. The nib of claim 9, wherein the plastic particles are selected from the group consisting of UHMWPE, VHMWPE and HDPE or a combination thereof.

12. The nib of claim 10, wherein the elastomeric particles are selected from the group consisting of ethylene-propylene copolymer, ethylene vinyl acetate (EVA), styrene-ethylene-butadiene-styrene (SEBS), hydrogenated SEBS and acrylonitrile-1,3-butadiene (NBR or nitrile rubber).

13. A porous sintered nib comprising:
a porous shank;
and,
a porous head,
wherein the shank has a first end to contact liquid in a reservoir and a second end to contact the porous head,
wherein the head has a body and a tip,
wherein the first end of the shank has an average pore size that is greater than an average pore size of the second end of the shank, and the body of the head has an average pore size that is greater than an average pore size of the tip of the head.

14. The nib of claim 13, wherein the shank and the head comprise plastic particles.

15. The nib of claim 13, wherein the head comprises plastic particles and elastomeric particles.

16. The nib of claim 14, wherein the plastic particles are selected from the group consisting of UHMWPE, VHMWPE and HDPE or a combination thereof.

17. The nib of claim 15, wherein the elastomeric particles are selected from the group consisting of ethylene-propylene copolymer, ethylene vinyl acetate (EVA), styrene-ethylene-butadiene-styrene (SEBS), hydrogenated SEBS and acrylonitrile-1,3-butadiene (NBR or nitrile rubber).

18. An applicator device comprising:
a housing;
a reservoir within the housing;
and,
the nib of claim 1, wherein the shank is located partially within the reservoir, the nub contacts an inner wall of the housing and the head extends beyond the wall of the housing.

19. An applicator device comprising:
a housing;
a reservoir within the housing;
and, the nib of claim 13, wherein the shank is located partially within the reservoir and contacts an inner wall of the housing and the head extends beyond the wall of the housing.

20. A method of applying a liquid containing high solids or pigments to a surface comprising:

exposing the shank of the nib of claim 1 to the liquid containing high solids or pigments in a reservoir;

permitting capillary force to move the liquid from the reservoir into the shank, through the shank into the nub, through the nub into the head and to the tip of the head;

contacting the tip of the head to the surface; and, permitting the liquid to flow from the tip of the head onto the surface.

21. The method of claim 20, wherein the surface is plastic, metal, paper, skin, hair, tissue or a wound.

22. The method of claim 20, wherein the liquid containing high solids or pigments is a cosmetic, a medicine, an adhesive, an ink, an antiseptic, an antibacterial, an antibiotic, or a liquid therapeutic agent.

23. A method of applying a liquid containing high solids or pigments to a surface comprising:

exposing the shank of the nib of claim 13 to the liquid containing high solids or pigments in a reservoir;

permitting capillary force to move the liquid from the reservoir into the shank, through the shank into the head and to the tip of the head;

contacting the tip of the head to the surface; and, permitting the liquid to flow from the tip of the head onto the surface.

24. The method of claim 23, wherein the surface is plastic, metal, paper, skin, hair, tissue or a wound.

25. The method of claim 23, wherein the liquid containing high solids or pigments is a cosmetic, a medicine, an adhesive, an ink, an antiseptic, an antibacterial, an antibiotic, or a liquid therapeutic agent.

* * * * *